United States Patent [19]

Bouton et al.

[11] Patent Number: 4,964,850
[45] Date of Patent: Oct. 23, 1990

[54] METHOD FOR TREATING TRANS-NASAL SINUS AFFLICTIONS USING A DOUBLE T-SHAPED TRANS-NASAL AERATOR

[76] Inventors: Vincent Bouton; Corine Bouton, both of 390 Avenue de Général Leclerc, Damarie Les Lys, France

[21] Appl. No.: 361,729

[22] Filed: Jun. 2, 1989

Related U.S. Application Data

[63] Continuation of Ser. No. 116,451, Nov. 3, 1987, abandoned.

[51] Int. Cl.$^5$ ............................................. A61M 31/00
[52] U.S. Cl. ........................................ 604/54; 604/8; 604/106; 606/108
[58] Field of Search ............... 604/283, 280, 281, 194, 604/8, 10, 49, 250, 48, 51, 54, 106, 156, 264; 128/305; 606/198, 199

[56] References Cited

U.S. PATENT DOCUMENTS

| | | | |
|---|---|---|---|
| 3,530,860 | 9/1970 | Majoros | 128/305 |
| 3,583,391 | 6/1971 | Cox | 604/280 |
| 3,592,197 | 7/1971 | Cohen | 604/280 |
| 3,645,268 | 2/1972 | Capote | 128/305 |
| 3,881,199 | 5/1975 | Treace | 604/280 |
| 3,897,786 | 8/1975 | Garnett et al. | 128/305 |
| 3,913,584 | 10/1975 | Walchle et al. | 128/305 |
| 3,948,271 | 4/1976 | Akiyama . | |
| 3,982,545 | 9/1976 | Silverstein . | |
| 4,015,607 | 4/1977 | Wright . | |
| 4,031,569 | 6/1977 | Jacob | 128/899 |
| 4,226,241 | 10/1980 | Walker, Jr. | 128/321 |
| 4,737,141 | 4/1980 | Spits | 604/28 |

FOREIGN PATENT DOCUMENTS 0063198 12/1981 European Pat. Off. .

OTHER PUBLICATIONS

Therapy of the Eustachian Tube, Zollner, Archives of Otolargngology, vol. 78, Sept. 1963, pp. 394-399 604/8.

*Primary Examiner*—C. Fred Rosenbaum
*Assistant Examiner*—Katheen H Daley
*Attorney, Agent, or Firm*—Lorusso & Loud

[57] ABSTRACT

A method for using a surgical apparatus that permits invisible and permanent drainage and aeration of chronically affected sinus passages in children and adults is disclosed. The apparatus is made of flexible plastic material, preferably of silicon or polyethylene. T-shaped wings located at the two extremities of a tube permit the apparatus to be held in position after insertion and to be with- drawn by means of pliers. The size of the aerator, its length and its wings can vary according to the age of the patient, the respective illness and the requirements of endoscopic control. Positioning of the aerator is accomplished by means of a delivery device in which the aerator is inserted with its wings folded. The aerator is pushed by means of a mandrel into the sinus up to a stop, whereupon the internal wings deploy; at this point it is necessary only to withdraw the delivery device to have the aerator in place.

6 Claims, 4 Drawing Sheets

METHOD FOR TREATING TRANS-NASAL SINUS AFFLICTIONS USING A DOUBLE T-SHAPED TRANS-NASAL AERATOR

This is a continuation of co-pending application Ser. No. 07/116,451 now abandoned filed on Nov. 3, 1987.

BACKGROUND OF THE INVENTION

The present invention relates to a surgical device that permits the permanent and invisible drainage and/or aeration of chronically or sub-acutely affected maxillary sinuses. The sinus is traditionally drained by means of a drain that exits from the narinary orifice. This allows the treatment for a period of from 7 to 15 days, but not on a permanent basis. It would be therefore desirable to provide a device allowing a permanent drainage of the sinus.

SUMMARY OF THE INVENTION

In one aspect, the invention provides a sinal aerator for permanently and invisibly draining maxillary sinuses and ventilating the latter in patients suffering from sub-acute or chronic affections. The aerator is characterized in that it comprises a hollow drain-type tube of a flexible plastic material introduced into the sinus to be treated. The tube straddles the bony wall separating the sinal cavity and the nasal canal, thus permitting communication between the cavity and the canal.

In another aspect, the invention provides a device for positioning the sinal aerator characterized in that it comprises a delivery device inside which is disposed a mandrel that permits the aerator to be slid in the sinal cavity until the internal wings open.

The aerator is small and cannot be seen except during rhinological examinations which must be performed by a specialist. The aerator may be left in its position during the time required to treat the sinal illness, up to several months, if necessary. Its installation, which requires the use of both hands, presents no difficulty to trained personnel.

According to a preferred embodiment of the invention, the aerator allows the physician to monitor by endoscopic means the state of the treated sinus. In a preferred embodiment the sinal aerator is manufactured of silicon or polyethylene.

DETAILED DESCRIPTION OF THE EMBODIMENTS

Figure 1:
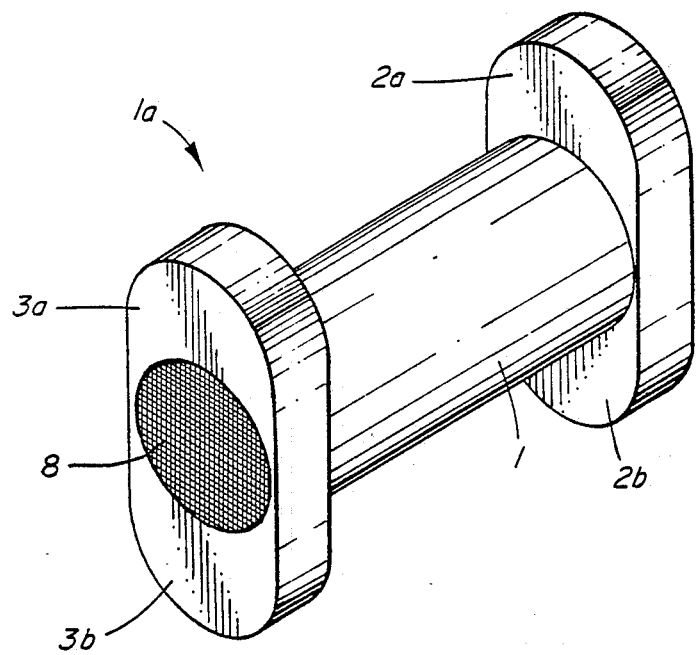
FIG. 1 is an enlarged perspective view of one preferred embodiment of the invention.

Referring to FIG. 1, the aerator comprises a hollow tube 1.5 mm in radius, 6 mm long and 0.5 mm thick. Two wings, 3a and 3b, are attached at one end of the tube. The wings are 1 mm thick and 3 mm long and open to an angle of 90°. When pressed against the internal face of the intersinuso-nasal wall 4 these wings produce a stopping effect which is responsible for holding the aerator in its installed position.

At the second end of the tube two identical wings, 2a and 2b are attached. These wings prevent the aerator from sliding into the sinus cavity, which might occur, for example, during blowing. The longitudinal axis of these wings is then disposed along the horizontal axis of the inferior nasal meatus. The wings, 2a and 2b, situated in the nasal canal permit additionally localization of the aerator and, when required, its withdrawal with a pair of standard prehensile pliers.

Depending on a particular embodiment, the length and the diameter of the tube may be reduced or increased. An increased internal diameter of the tube permits introduction of an instrument of endoscopic control into the sinal cavity. Similarily, the number, length and thickness of the wings may be changed to suit the age of the person treated, particularities of the illness and personal preferences of the staff administering the treatment. The angle at which the wings are attached to the tube may vary, thus permitting the aerator to be inclined toward the rear. Such positioning simplifies the ventilation of the treated sinus by warm air expired through the nose.

An obturative membrane 8 impervious to water but permeable to air may close the tube at its nasal orifice. This embodiment permits bathing, swimming and other water activities.

Figure 2:
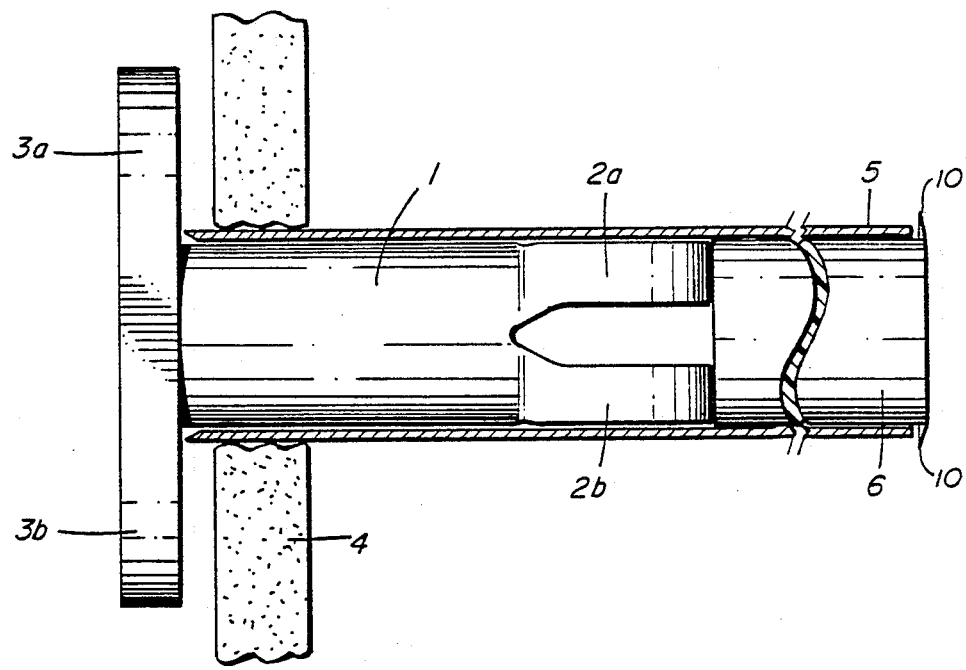
FIG. 2 is a cross-sectional view of one preferred delivery and positioning device.
Figure 3:
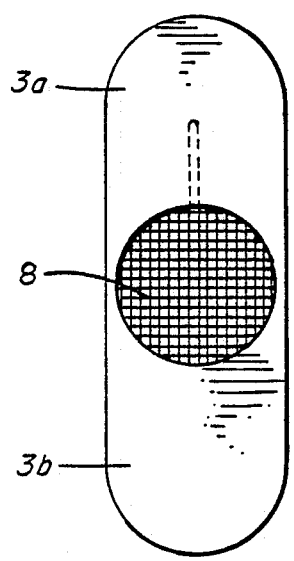
FIG. 3 is an enlarged front view of one preferred embodiment of the invention.

Referring to FIG. 2, the positioning device of the invention consists of a delivery device 5 that permits the perforation of the bony wall 4 separating the sinus from the nasal canal, through which the operation takes place without sight control. This action is performed as a "sinus puncture" in the inferior nasal meatus. Prior to the positioning the aerator is placed by the operator inside the delivery device with the wings folded. The positioning device comprises a mandrel 6 disposed inside the delivery device 5 so as to permit the aerator to be slid forward until the internal wings deploy. A stopping device assures the operator advancing the mandrel that the sinus aerator is properly positioned and that any further advancement of the mandrel is undesirable. In this manner the aerator is prevented from being pushed too far and irretrievably lost in the sinus cavity. A fin-type device 10 stops the movement of the mandrel inside the delivery device at the moment when the fin meets the end of the slit designed to admit the internal wings and a portion of the aerator tube into the desired position. Once the internal wings have been deployed and the stop prohibits further progress, the operator withdraws the delivery device; the aerator is kept in position by the internal wings resting against the internal face of the bony wall; the delivery device slides along the aerator. When the latter is entirely freed, the external wings deploy.

Figure 4:
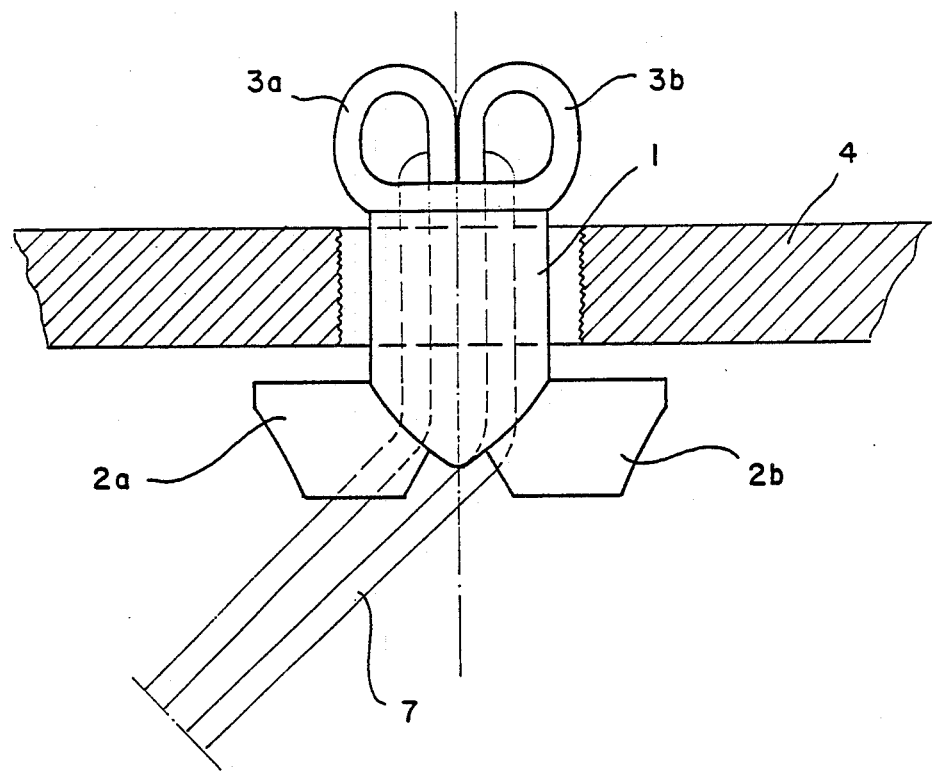
FIG. 4 is a view of the aerator with another preferred positioning device, prior to the positioning.
Figure 5:
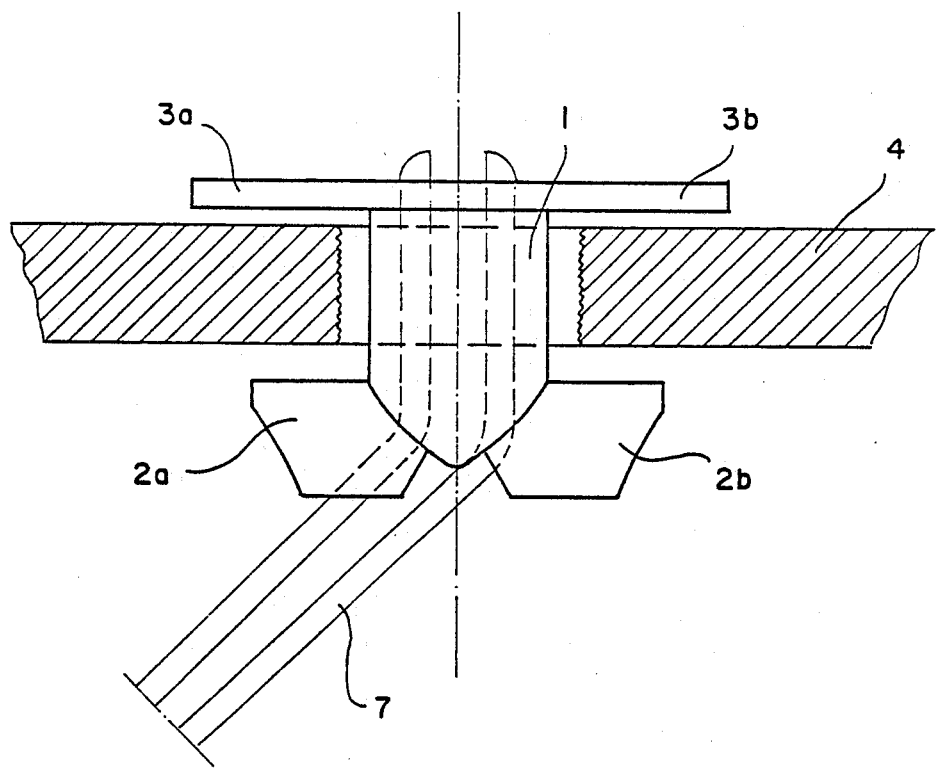
FIG. 5 is a view corresponding to FIG. 4, after the positioning.

According to another embodiment of the invention the positioning device comprises a bent pliers inserter 7 slid inside the tube 1 of the drain to grasp the internal wings 3a and 3b and keep them in the undeployed position (FIG. 4). The pliers-drain assembly is placed in the orifice created with the help of the delivery device 5, the external wings 2a and 2b of the drain helping to create a stop which limits the advance of the aerator during the operation. At this moment, the nasal canal is endoscopically examined, then the jaws of the pliers are opened, to permit the internal wings to deploy inside the sinus (FIG. 5). Subsequently, the jaws of the pliers are brought together to permit the withdrawal of the pliers, which are then gently slid out of the drain which is held in place by the positioning of the deployed internal wings. From this time, the device according to the invention is in place.

In any embodiment, the wings do not deploy due to any specific mechanism. Their final disposition results from the fact that they have been moulded in their respective positions and from the characteristics of the material used in their manufacture.

The embodiments of the invention in which an exclusive property or privilege is claimed are defined as follows:

1. A method for draining and ventilating maxillary sinuses in patients suffering from sub-acute or chronic affections, comprising the steps of:
    perforating the bony wall separating a sinal cavity from a nasal passage to provide an opening in the bony wall;
    providing a hollow drain tube made of flexible plastic material with flexible wings attached at each end, wherein said wings permit unidirectional passage of the tube through an opening to allow insertion of the hollow drain tube through the opening in the bony wall and to retard movement of the hollow drain tube once positioned in the bony wall;
    inserting said hollow drain tube with positioning means until the wings on one end of said hollow drain tube pass through the perforated bony wall and into the sinal cavity;
    deploying wings on the end within the sinal cavity thereby locking said hollow drain tube on the sinal cavity side on said bony wall; and
    withdrawing the positioning means from the bony wall, said withdrawing liberating the wings in an open position to lock the hollow drain tube in place on the nasal passage side of the bony wall and provide a fixed draining and ventilating means between the sinal cavity and nasal cavity.

2. A method according to claim 1 further comprising the step of closing the wings on one end of the hollow drain tube before inserting said hollow drain tube through the opening in the bony wall.

3. A method according to claim 2, wherein said wings remain closed until said positioning means is removed from the bony wall, causing the wings on each end to open and lock the hollow drain tube in place.

4. A method according to claim 2, wherein said hollow drain tube is inserted through a temporary drain tube positioning device to the point at which the wings at one end of the hollow drain tube pass beyond the temporary drain tube positioning device and open.

5. A method according to claim 1 wherein said hollow drain tube is inserted into said opening in the bony wall with bent pliers which extend through the hollow drain tube and grasp the wings at one end to hold them in a compressed state.

6. A method for draining and ventilating maxillary sinuses in patients suffering from sub-acute or chronic affections, comprising the steps of:
    perforating the bony wall separating a sinal cavity from a nasal passage to provide an opening in the bony wall;
    providing a hollow drain tube made of flexible plastic material with flexible wings attached at each end, wherein said wings permit unidirectional passage of the tube through an opening to allow insertion of the hollow drain tube through the opening in the bony wall and to retard movement of the hollow drain tube once positioned in the bony wall;
    closing the wings on one end of the hollow drain tube by compressing the wings with bent pliers before inserting said hollow drain tube through the opening in the bony wall;
    inserting said hollow drain tube with said bent pliers wherein said wings remain closed until the wings on one end of said hollow drain tube pass through the perforated bony wall and into the sinal cavity;
    deploying wings on the end within the sinal cavity thereby locking said hollow drain tube on the sinal cavity side on said bony wall; and
    withdrawing the bent pliers from the bony wall, said withdrawing liberating the wings in an open position to lock the hollow drain tube in place on the nasal passage side of the bony wall and provide a fixed draining and ventilating means between the sinal cavity and nasal canal.

* * * * *